United States Patent [19]
Gruber

[11] 4,299,128
[45] Nov. 10, 1981

[54] ULTRASONIC SATELLITE-PULSE TECHNIQUE FOR CHARACTERIZING DEFECTS OF ARBITRARY SHAPE

[76] Inventor: George J. Gruber, P.O. Box 28510, San Antonio, Tex. 78284

[21] Appl. No.: 142,216

[22] Filed: Apr. 21, 1980

[51] Int. Cl.$^3$ .......................................... G01N 29/04
[52] U.S. Cl. .................................................. 73/627
[58] Field of Search ................ 73/627, 628, 629, 620, 73/1 DV

[56] References Cited

U.S. PATENT DOCUMENTS

| | | | |
|---|---|---|---|
| 3,592,052 | 7/1971 | Di Giacomo | 73/620 |
| 4,137,779 | 2/1979 | Wüstenberg et al. | 73/627 |

FOREIGN PATENT DOCUMENTS

| | | | |
|---|---|---|---|
| 1448471 | 9/1976 | United Kingdom | 73/627 |

OTHER PUBLICATIONS

R. Frielinghaus et al., "Problems Associated With Ultrasonic Reference Defects," *Non-Destructive Testing*, pp. 125–127, Apr. 1970.

M. G. Silk, "Sizing Crack-Like Defects By Ultrasonic Means," *Research Techniques in Non-Destructive Testing*, vol. III, Chap. 2, pp. 51–99, 1977.

*Primary Examiner*—Stephen A. Kreitman
*Attorney, Agent, or Firm*—Gunn, Lee & Jackson

[57] ABSTRACT

A nondestructive testing method of ultrasonic defect characterization based upon the separation in time-of-arrival between the reflected pulse and its leading diffracted satellite pulse in the case of a crack-like defect and its lagging scattered satellite pulse in the case of an inclusion-like defect is shown. The angle beam, single probe type, echo ranging technique differentiates the main defect reflection from the satellite pulses of the defect and uses the sequence and magnitude of the separation in time-of-arrival between the pulses to determine the shape and size of the defect. Due to a discovered linear relationship between the ultrasonic delay time and defect size, the time scale of an oscilloscope's screen can be adjusted to read directly in terms of crack depth or inclusion diameter. Beyond the need to recognize returning pulses, the relationship is independent of wave amplitudes and the technique is thus easily utilized and is compatible with many different types of materials to be tested.

29 Claims, 14 Drawing Figures

ULTRASONIC SATELLITE-PULSE TECHNIQUE FOR CHARACTERIZING DEFECTS OF ARBITRARY SHAPE

BACKGROUND OF THE INVENTION

This invention relates to ultrasonic nondestructive testing and, more particularly, to a test method which is able to identify defects and determine orientation and size via a pulse analysis method.

Current nondestructive testing methods for metal weld and high pressure containment vessel defects fail to provide sufficient information upon which satisfactory fracture mechanics lifetime—prediction models can be predicated. This is due to the demand for more valid and reliable defect characteristics information occasioned by nuclear generating plants and the severe physical constraints encountered in attempting to provide such information. Useful quantitative information about the characteristics of the defect may be obtained by peak-amplitude, arrival-time, or frequency-content analysis.

Because small defects in areas of high mechanical or thermal stress may affect the service strength of the parts sufficiently to warrant rejection, and because measurement of the peak amplitude of the principal defect echo is unreliable for small defects, a new nondestructive testing technique is required.

An additional problem encountered by many conventional ultrasonic tests is the need for extensive calibration of the apparatus for the testing of any part. It is also difficult to repeat these tests to determine in-service progression of the defects so it can be determined whether the defect is "malignant" (propagating) or "benign" (non-propagating).

Included as representative of the state-of-the-art, "Problems Associated With Ultrasonic Reference Defects", R. Frielinghaus, J. Krauthramer and U. Schlengermann, *Non-Destruction Testing*, April 1970, pages 125–27; "Sizing Crack-Like Defects by Ultrasonic Means", M. G. Silk, *Research Techniques In Nondestructive Testing*, 1977, Volume III, pages 51–99; and U.S. Pat. No. 4,137,779, "Methods and Arrangement for the Determination of Crack-Depths in Ultrasonic Nondestructive Testing" by H. Wustenberg and E. Schulz, filed Dec. 7, 1973. Additionally, a paper entitled "Defect Identification And Sizing By The Ultrasonic Satellite-Pulse Technique" which was delivered to the Advanced Research Project Agency/Air Force Review of Progress in Quantitative NDE during July 8–13, 1979 by the inventor is included.

Frielinghaus discusses the fact that ultrasonic characterization of reference defects is complicated by the existence of scattered waves. While some attempt is made therein to discuss the composition of an echo from a sawtooth groove, no attempt is made at deriving information concerning the defect itself.

Silk completely ignores inclusion-like defect characterization as is described in the current invention. It further does not deal with directly diffracted or scattered satellite pulses produced and recorded by a single probe. The publication, in fact, teaches away from the present invention stating that "The single probe approach seems to be less accurate than the transmission approach, because of the weak reflection from the crack tip in many cases and the presence of other interferring pulses arising from defect irregularities; mode conversion, etc." Id. at 83. The present invention surmounts those difficulties. The Silk publication further does not disclose any means of self-calibration or direct-readout capability.

Wustenberg teaches directly away from the present invention in that it utilizes the defect as a sound beam stop rather than as an echo pulse producer. Wustenberg "ascertain[s] the depth propagation of the defect by a marked increase in intensity of the received signal when the intersection of the respective lines along which the ultrasonic wave is transmitted and the scatter signal is received reach beyond the innermost limits of the defect." Id. at page 4, lines 54–58. The Wustenberg method thus requires two separated probes to find a point immediately below the defect. The use of the term "scatter signal" as used therein identifies waves diffracted at structural inhomogeneities as opposed to circumferential scattering due to defect surface wave radiation.

SUMMARY OF THE INVENTION

The object of the present invention is to provide means of anomaly or defect characterization which is new and noval in the nondestructive testing field. It is an object that the invention be generally applicable whenever the need for determining nondestructively the shape and size of an anomaly or a defect arises.

It is a further object to provide a nondestructive anomaly identification and sizing technique which is independent of return pulse amplitudes, anomaly location and operating frequency.

It is a further object to provide a single probe technique which is self-calibratable and has direct readout capability.

The invention method and arrangement for defect or anomaly identification and sizing operates by utilizing generally discarded satellite pulses created during ultrasonic testing. It has been discovered that by detecting, resolving, and recognizing the extra pulses created due to ray splitting at the defect "extremities", useful information can be obtained. Because the method depends only upon resolving returning pulses, detecting the pulses and measuring the times-of-arrival of the pulses, the technique is practically independent of pulse amplitudes. Pulse amplitude is sufficient if it allows detection and resolution of the pulses. Upon investigation, it was found that tangentially-scattered pulses contain significant size information about volumetric defects. For void-like defects, a pair of surface waves or "creeping waves" are created upon the surface of the defect by the incident ultrasonic wave upon the defect. The bulk wave to surface wave mode conversion occurs at 90 degrees from the point of specular reflection and the surface waves travel about the defect with the Rayleigh velocity rather than the bulk velocity. As the surface waves circumferentially bound the defect, a surface-wave-to-bulk-wave reconversion occurs due to tangential radiation. At certain points about the volumetric defect, the tangentially-radiated bulk wave is directed toward an ultrasonic receiving probe and a detectable return pulse is recorded. When the time-of-arrival of the lagging small tangentially-scattered pulse is compared to that of the main front-reflected pulse upon a calibrated oscilloscope, directly readable data giving the diameter of the defect is shown thereon. The difference between the time-of-arrival of a satellite pulse and the time-of-arrival of its associated main reflected pulse is quantified as the "delay time" between the pulses.

Similarly, for a crack-like defect, the time-of-arrival of the leading small tip-diffracted component of the returning pulse pair may be compared to that of the main base-reflected wave component to give data needed for sizing the planar defect. Due to improvements and refinements discussed below, the invention is self-calibrating, utilizes a single probe, is independent of pulse amplitude, operating frequency, wave mode, and defect location, and it produces a direct readout due to the linearity of defect size versus delay time relationships.

DESCRIPTION OF THE PREFERRED EMBODIMENT

The preferred embodiment and best mode of the invention involves use of an ultrasonic method to identify and size planar crack-like defects or anomalies and volumetric inclusion-like defects or anomalies in metals. It is to be understood, however, that virtually any type of anomaly in virtually any type of medium can be substituted as the target to be identified and sized as is described and claimed herein. Further, the method is not limited to ultrasonic waves, but rather other types of wave motion can be utilized where practicable. The described method produces physical representations of the targeted defect's shape and size. The method of explanation herein has been chosen to permit those skilled in the art of nondestructive testing to readily use it.

"Satellite pulse" as used herein is defined to mean the pulse corresponding to tip diffraction or tangential scattering produced by an incident ultrasonic wave interacting with an anomaly within a body. It is understood that the discussion below concerning anomalies with a simple geometry is merely illustrative of the Satellite-Pulse Technique's applicability to anomalies having complex shapes. To identify and size an anomaly having a complex geometry and more than one satellite pulse, each representing a certain tip-diffracted wave or a certain tangentially-scattered wave, may be used by adopting the methods described below.

The tools and equipment employed in this technique generally comprises a transducer, a plastic shoe or wedge, a transmitter, a receiver, and a resolution unit (wave time-of-arrival device) such as an oscilloscope.

Because the waves transmitted and received in nondestructive testing are generally generated and observed as electronic signals, they are referred to in the industry as "pulses". "Scattered waves" are defined as waves which have been created due to mode conversion from an incident bulk wave to surface wave and have been reradiated. "Back scattered waves" are defined as the scattered waves resulting from incident-wave-induced circumferential surface waves traveling from a point of incident wave impingement upon the anomaly to at least one anomaly location to which scattered waves are tangentially reradiated by the anomaly.

The detected wave components resulting from interaction of the ultrasonic beam with the defect are detected by a transducer and the data displayed upon an oscilloscope. A satellite pulse therefore is the electrical signature of a satellite wave, a reflected pulse is the electrical signature of a reflected wave, and so on. Amplitude of such pulses is further the electronic measure of the energy content of the wave components and reception times of the pulses are the reception times (time-of-arrival) of the wave components.

Initial location of a defect may be made by any of a number of conventional methods. Step 1 of the satellite-pulse technique involves the detection, resolution, and recognition of a satellite associated with the main reflected pulse if such a satellite pulse exists. Step 2 of the Satellite-Pulse Technique involves identifying the detected defect as either "planar" (crack-like) or "volumetric" (inclusion-like) from the preliminary data received. Step 3 of the Satellite-Pulse Technique involves characterizing the identified defect according to size and orientation.

A transducer is used to convert short electrical pulses into an incident beam of ultrasonic waves which are transmitted into the body being tested. The specularly-reflected pulse is normally easily recognizable due to its large amplitude relative to other returning pulses. Upon the incident beam being properly aimed at the defect's extremeties to permit detection and resolution of the satellite pulses, the defect can be identified. Aiming the probe comprises judiciously moving it about the general area of the previously located defect; firstly to detect and resolve the satellite pulse; secondly to recognize it; and thirdly to maximize it. This may be accomplished while using either fixed angle or variation angle probes. Sufficient detection and resolution are attained by transmitting short pulses, resolving the returned pulses with a high resolution receiver, and placing the probe at such a distance and angle with regard to the defect that the satellite pulses have an appreciable amplitude above the general interference background normally present (due to the microstructure of the tested body itself creating unpredictable fluctuations in the received signal). Recognition of a pulse as a satellite pulse is normally achieved by varying the location of the probe about the defect and comparing the pulse patterns received from neighboring examination volumes in a manner described below as "satellite-pulse pattern recognition."

Crack-like defects having a sharp tip act as an edge diffractor of sound and are categorized as planar defects. Typical crack-like defects produce a pair of echoes (pulse pair); a base-reflected pulse and a tip-diffracted pulse. The satellite pulse created by proximal tip diffraction precedes the stronger primary pulse due to reflection and the delay time between the reflected and diffracted pulses will vary linearly with size of the defect but nonlinearily with its orientation angle with regard to the incident beam.

Porosities, voids, and other inclusion-like defects having a smooth back surface act as a scatterer of sound and are categorized as volumetric defects. The pulse pairs produced by volumetric defects are due to the front-reflected and back-scattered waves. In contrast to planar defects, the pulse created by the tangential reradiation from the back side of the volumetric defect follows the stronger reflected pulse and the delay time between the associated pulses from a volumetric defect does not vary significantly with the bearing angle of the incident beam.

Ghost satellites are pulses associated with the main reflected pulse which may be mistaken for a true satellite pulse but is not a true satellite pulse. A ghost satellite pulse is distinguishable from the general interference background as an associated pulse of the main reflected pulse. Use of a satellite-pulse pattern recognition method is necessary to recognize such pulses as ghost pulses distinguished from satellite pulses. Pulses which vary in amplitude and time-of-arrival as a function of the changing amplitude and time-of-arrival of the main reflected pulse upon changing the position of the probe or the bearing angle of the incident beam are true associated pulses and are thus distinguishable from general background interference.

The first step of the satellite-pulse technique involves the detection, resolution, and recognition of the satellite pulse associated with a main reflected pulse if such a pulse exists. If the only pulses except for the main reflected pulse and general background interference are ghost pulses (i.e., no satellite pulses are present) then the main reflected pulse is not being caused by a defect but is due to the geometry of the tested material. If satellite pulses do exist, then the main reflected pulse is associated with a defect or anomaly of some type within the tested material and further testing is necessary.

Figure 1:
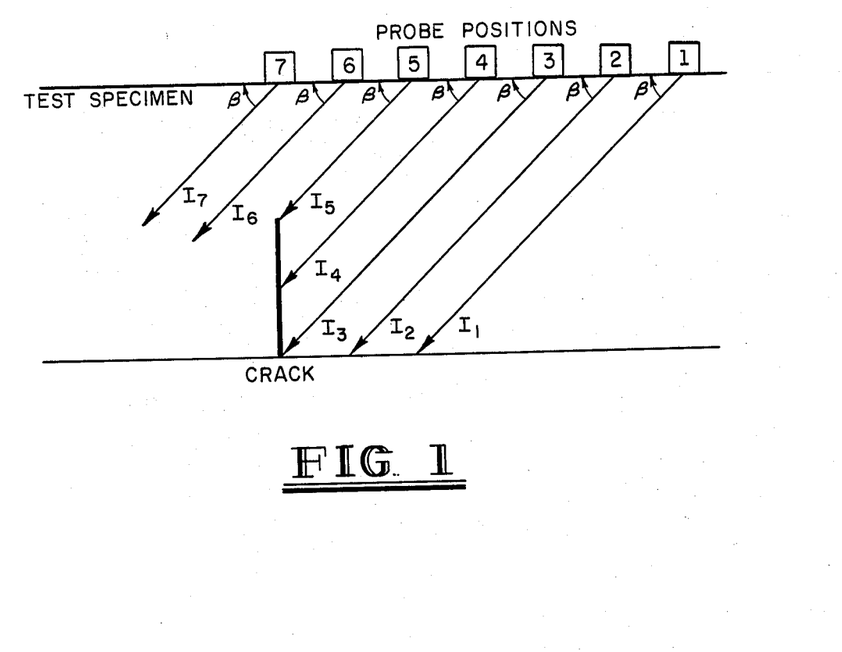
FIG. 1 shows various possible probe positions upon a test specimen with regard to a crack-like defect upon the far surface of the test specimen. The probe emits an incident ultrasonic beam I, the center of each beam I corresponding to a numbered probe position as shown and additionally being labeled with a number indicating the probe position. The bearing angle $\beta$ for each incident beam is identical.
Figure 2:
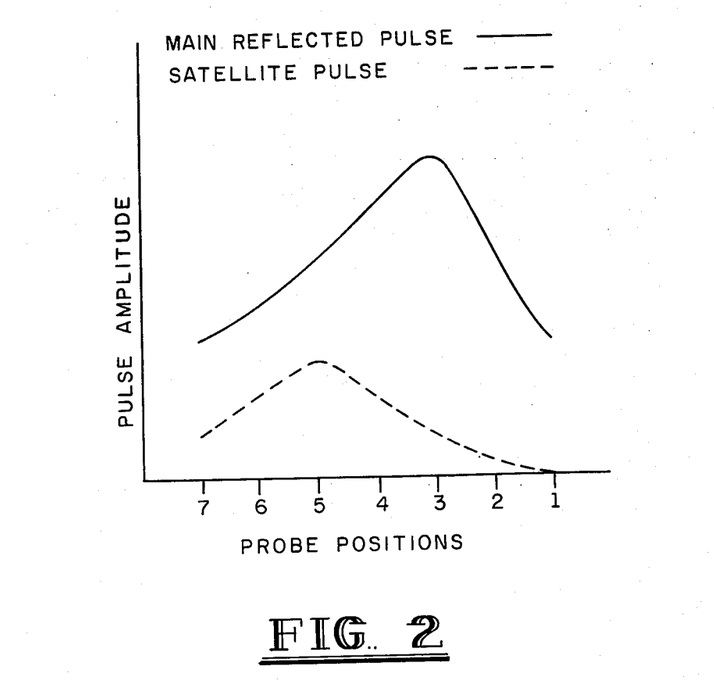
FIG. 2 shows the relative pulse amplitudes of the main reflected pulse and the satellite pulse associated with a crack-like defect upon being insonified by a probe located and having bearing angles as shown in FIG. 1.
Figure 3:
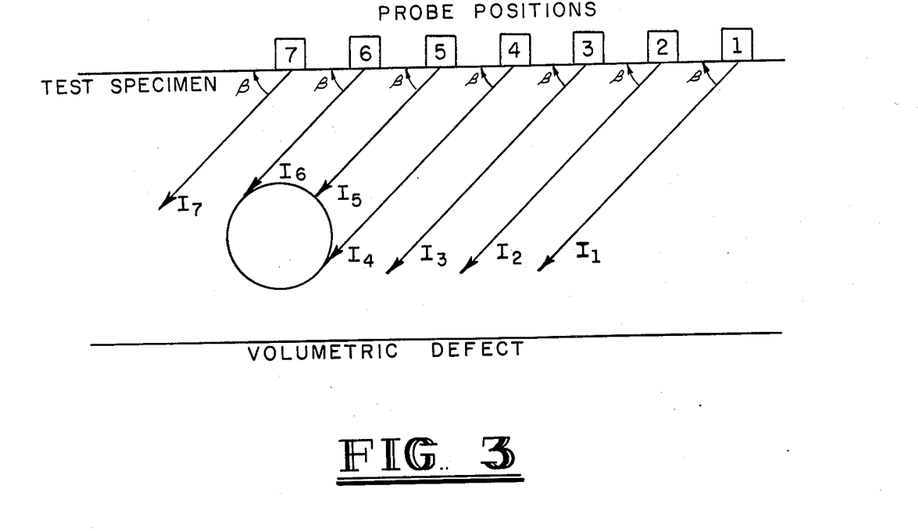
FIG. 3 shows various possible probe positions upon a test specimen with regard to a volumetric defect. The probe emits an incident ultrasonic beam I, the center of each beam I corresponding to a numbered probe position as shown and additionally being labeled with a number indicating the probe position. The bearing angles $\beta$ for each incident beam are identical.

FIG. 1 shows 7 probe positions with reference to a planar defect and FIG. 2 shows relative returning pulse amplitudes for the main reflected pulse and the associated satellite pulse for the defect and probe positions as shown in FIG. 1. FIG. 3 shows 7 probe positions with reference to a volumetric defect and FIG. 4 shows the relative returning pulse amplitudes for the main reflected pulse and the associated satellite pulse for the defect and probe positions as shown in FIG. 3.

While current ultrasonic tests counsel maximization of the amplitude of the main reflected pulse, the satellite-pulse technique sacrifices the main reflected pulse's amplitude to maximize the amplitude of the sought after satellite pulse. As shown in FIG. 2 and FIG. 4, characteristic satellite-pulse patterns are produced by defects of various shape which, together with the other defect signatures as described above, permit the differentiation of real satellites from ghost pulses and general background interference.

For example, a pulse may be a suspected satellite pulse because it precedes and is associated with the main reflected pulse. In this instance, the applicable relative amplitude pattern between the suspected satellite pulse and the main reflected pulse must be similar to the dissynchronous relative amplitude pattern shown in FIG. 2 for the suspected satellite pulse to be a true satellite pulse. A pulse whose time-of-arrival precedes the main reflected pulse and which does not have a dissynchronous relative amplitude pattern similar to that shown in FIG. 2 is a ghost satellite or is due to general background interference.

Figure 4:
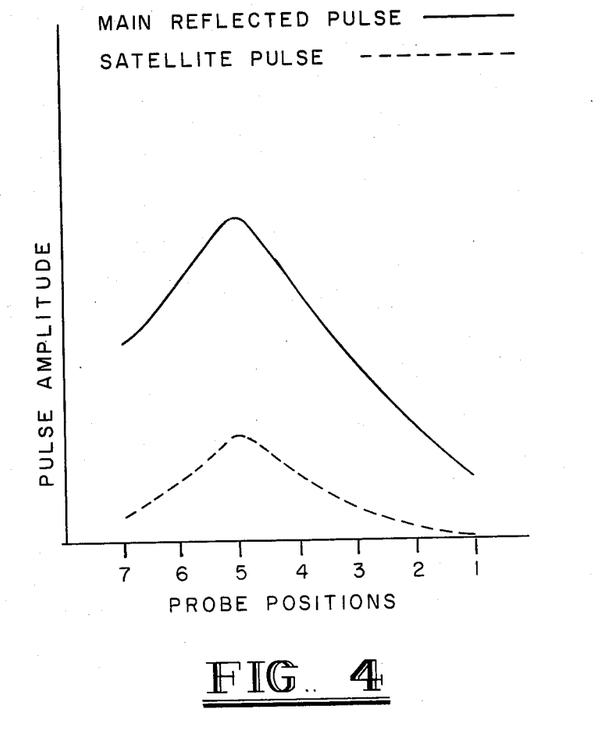
FIG. 4 shows the relative pulse amplitudes of the main reflected pulse and the nearest satellite pulse associated with a volumetric defect upon being insonified by a probe located and having bearing angles as shown in FIG. 3.

By the same token, a pulse received subsequent to the main reflected pulse must have a synchronous relative amplitude pattern similar to that shown in FIG. 4 or it is not a satellite pulse.

The synchronous pattern composed of the main reflected pulse and its lagging satellite pulse is a signature of volumetric defects and the dissynchronous pattern composed of the main reflected pulse and its leading satellite pulse is a signature of planar defects. It is seen that these represent the synchronous relative energy content pattern and the dissynchronous relative energy content pattern of the tested volumetric defect and planar defect, respectively.

It is seen that time-of-arrival of the main reflected pulse reflected to the time-of-arrival of the main reflected pulse is used to select which relative amplitude pattern the suspected satellite pulse must be similar to in order to determine it to be a true satellite pulse. Thus the relative amplitude pattern signature is used to recognize the pulse as a satellite pulse. This method of selecting and identifying true satellite pulses is satellite-pulse pattern recognition. There may be more than one satellite pulse derived from defects depending upon defect geometry but the same process of elimination herein described is applicable for the testing of each suspected satellite pulse.

Implicit in satellite-pulse pattern recognition is the need to produce and observe at least two pairs of pulses (a pair comprising the primary specularly-reflected pulse and the secondary satellite pulse) by moving the probe to at least two different positions about the defect. The particular set of two pulse pairs produced to achieve satellite-pulse pattern recognition is a physical representation of the identity or type (as either planar or volumetric) of the defect. These particular two pulse pairs are neither purposefully produced nor purposefully recorded except upon use of the satellite-pulse technique. Further, comparison of the particular patterns thus produced with the planar and volumetric defect identification patterns described above is unique to the satellite-pulse technique.

Maximization of the satellite pulse facilitates and is often necessary for satellite-pulse pattern recognition. As stated above, the satellite pulses are generally relatively weak return signals and, in the case of planar defects, are normally not identifiable when the incident beam is aimed at the base of the crack as in FIG. 1 probe position 3. As shown in FIG. 2, it is necessary to move the probe past probe positions 3 and 4 to maximize the amplitude of the satellite pulse. At probe position 5, the center of the incident beam is directed toward the upper extremity of the planar defect. If an angle beam probe is placed directly above the defect, the satellite pulse will again recede into the general background interference. To maximize the satellite pulse amplitude therefore, the operator will typically move the probe towards the defect through probe positions 1–5 and until he detects the amplitude decreasing at positions 6 and 7. By judiciously thus varying the probe location, the satellite pulse amplitude may be maximized.

Because the amplitude of the primary, specularly-reflected pulse is normally many times greater than any other received pulse, its amplitude can generally be sacrificed after it has been recognized. Maximization of satellite pulses is not purposefully undertaken in any defect identification and subsequent sizing method except the satellite-pulse technique. This physical representation of the defect produced by maximizing the amplitude of the secondary satellite pulse at the expense of the amplitude of the primary, specularly-reflected pulse is unique to the satellite-pulse technique.

Upon recognition of the satellite pulse, the defect may be identified as being either planar or volumetric upon varying the probe's position relative to the defect and comparing the detected pulse patterns to the two described above. If the time-of-arrival of the satellite pulse precedes the time-of-arrival of the main reflected pulse the defect is planar and if it is subsequent to the time-of-arrival of the main reflected pulse the deflect is volumetric. Comparing the actual relative amplitude patterns with the expected relative amplitude pattern of FIG. 2 or 4, as applicable, confirms the identification.

Another method of distinguishing planar from volumetric defects is by varying the bearing angle of the probe. Varying the bearing angle of the incident beam from a first bearing angle to a second bearing angle and moving the probe from its first position to a second position from which the incident beam will contact the defect at the same location as before will not cause a significant change in either relative amplitudes or in the delay times between the time-of-arrival of the satellite pulse and the main reflected pulse for a volumetric type defect. If the defect is crack-like, however, the relative amplitudes and the delay times will each vary significantly and nonlinearly with the bearing angle change.

This broad classification of defects into planar crack-like defects and volumetric inclusion-like defects as the second step allows separate defect identification and sizing techniques to be conjunctively or alternatively used to characterize defects of almost any shape. By using such a stepwise approach, the single general defect characterization technique permits full evaluation of almost any defect.

The third step is to describe the defect more fully by determining its characteristics beyond location and type. If the defect has been identified as volumetric, then one method of defect characterization will be used; and if planar, then another method will be used. As a matter of convenience, use of the satellite-pulse technique for sizing volumetric defects will be described first and the use of the satellite-pulse technique for sizing crack-like defects will be described second.

Figure 5:
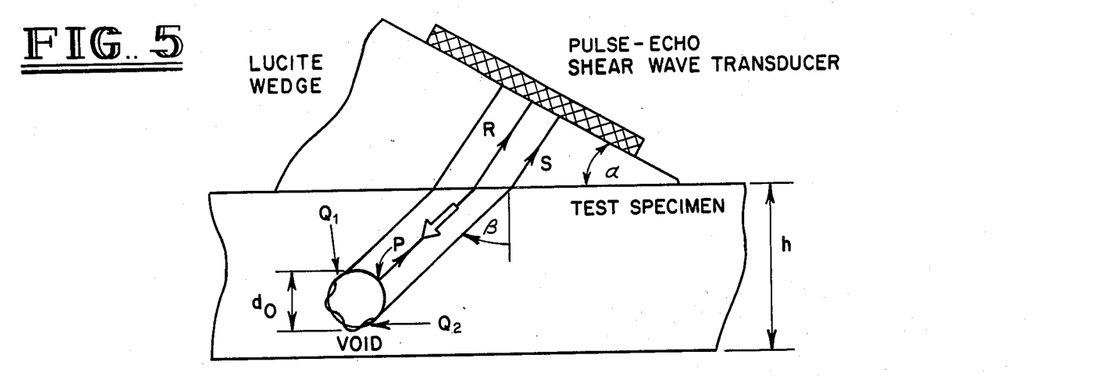
FIG. 5 shows the interaction of an ultrasonic shear wave having a bearing angle $\beta$ in a test specimen of thickness h with a void-like defect having a diameter $d_o$. The incident wave (hollow arrow) contacts the void at point P to produce a specularly-reflected component R and contacts the void at points $Q_1$ and $Q_2$ to produce a lagging tangentially-scattered component S. The "R-wave" is reflected at point P and the "S-waves" are radiated at points $Q_1$ and $Q_2$. The lucite wedge of inclination angle $\alpha$ and transducer are known tools.

FIG. 5 shows a validated model of the interaction of an ultrasonic shear wave with a void in metal. An oversimplified model of this interaction assumes that the speed of the "creeping wave" along the void's periphery is identical to that of the longitudinal bulk wave $c_p$ rather than that of the Rayleigh surface wave. This yields an invalid expression for the separation in time-of-arrival of the specularly-reflected and first pair of scattered pulses $\Delta_o$ in terms of the void's diameter $d_o$ as shown below:

$$\Delta_o = \frac{2.57 d_o}{c_p} \qquad (1)$$

Figure 6:
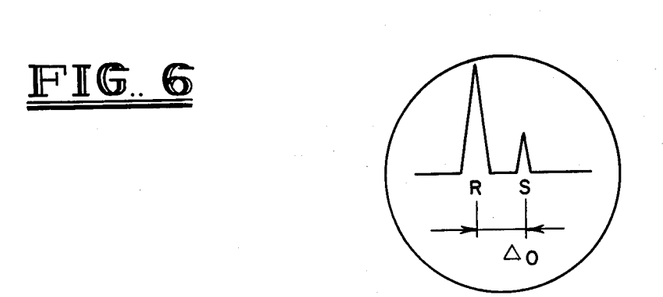
FIG. 6 shows the reflected pulse R and scattered pulse S separated by delay time $\Delta_o$ on an oscilloscope screen due to ray splitting by the void of FIG. 5.

As shown in FIGS. 5 and 6, in the defect-sizing position (probe position 5 in FIG. 3) the incident ultrasonic beam is aimed at the center of the void to maximize the amplitude of the first pair of creeping waves which arrive at the pulse-echo shear wave transducer simultaneously after having traveled ("crept") once around the back surface of the void in opposite directions. For clarity, only the counterclockwise creeping wave is shown by the wiggly line from $Q_1$ to $Q_2$ in FIG. 5. When the ultrasonic wave encounters the front surace of the void at point P, a specularly-reflected wave ("R-wave") is sent back to the transducer (front reflection). A pair of Rayleigh-type surface waves is also produced by the incident wave at points $Q_1$ and $Q_2$. These Rayleigh waves circumvent the hole a number of times until they disappear into the background interference since their energy is continuously depleted by tangential radiation. Each time the counterclockwise creeping wave reaches point $Q_2$, the tangential reradiation, in the form of a tangentially-scattered wave ("S-wave") from the hole during its circumvention, is launched at the desired detection angle to be received by the transducer (back scattering). The delay time $\Delta_o$ between the R pulse and its first scattered satellite S as shown in FIG. 6 is a linear function of the diameter of the void $d_o$ as expressed by the relationship $$\Delta_o = \left(\frac{\pi}{2v} + \frac{1}{c}\right) d_o \quad (2)$$

where c is the shear wave velocity and v is the Rayleigh wave velocity of the test specimen. This equation differs from Equation (1) in that the creeping wave travels along the defect's periphery with the Rayleigh velocity (rather than the bulk velocity). For carbon steel 1020, Equation (2) becomes $$c\Delta_o = 2.71 d_o \quad (3)$$

The constant of this equation differs from that of Equation (1) (i.e., 2.57) and its validity is born out by experimental results.

The first two reflections from the test specimen's end, or from the end of a plate similar composition, may be used to eliminate the influence of the generally unknown shear wave velocity on the linear relationship between $d_o$ and $\Delta_o$ in Equation (3).

Figure 7:
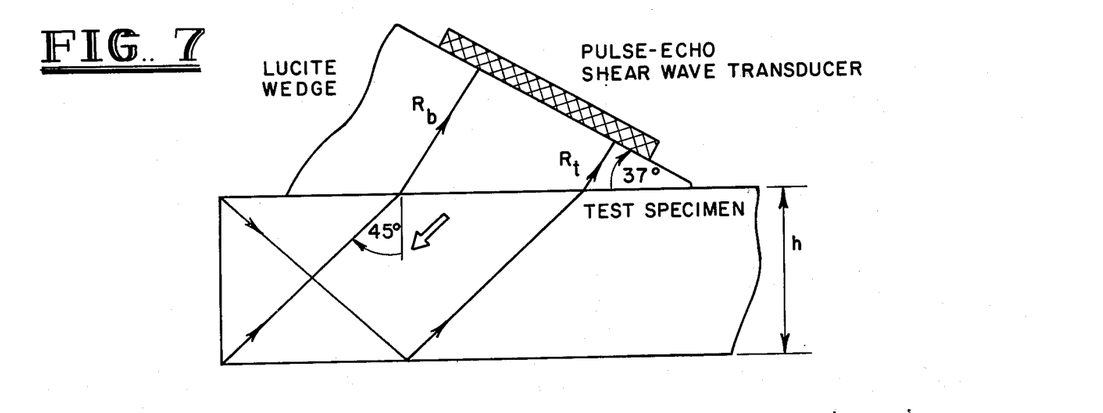
FIG. 7 shows the splitting of a 45-degree incident wave (hollow arrow) into a bottom-reflected wave $R_b$ and a top-reflected wave $R_t$ by the end of a carbon steel plate as occurs during self-calibration of the horizontal scale of the oscilloscope for direct readout of defect size.
Figure 8:
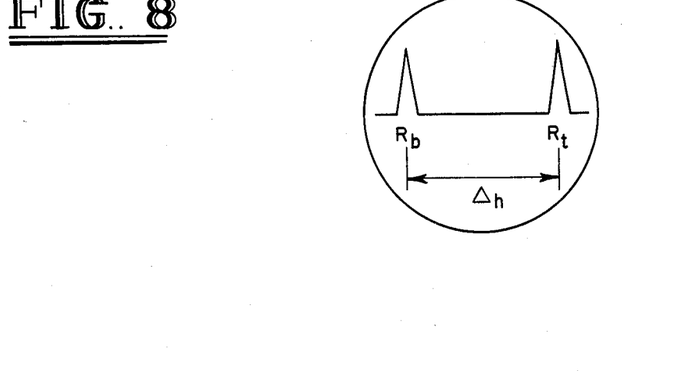
FIG. 8 shows the bottom and top-reflected pulses $R_b$ and $R_t$, respectively, separated by the calibration delay time $\Delta_h$ on the oscilloscope screen.
Figure 9:
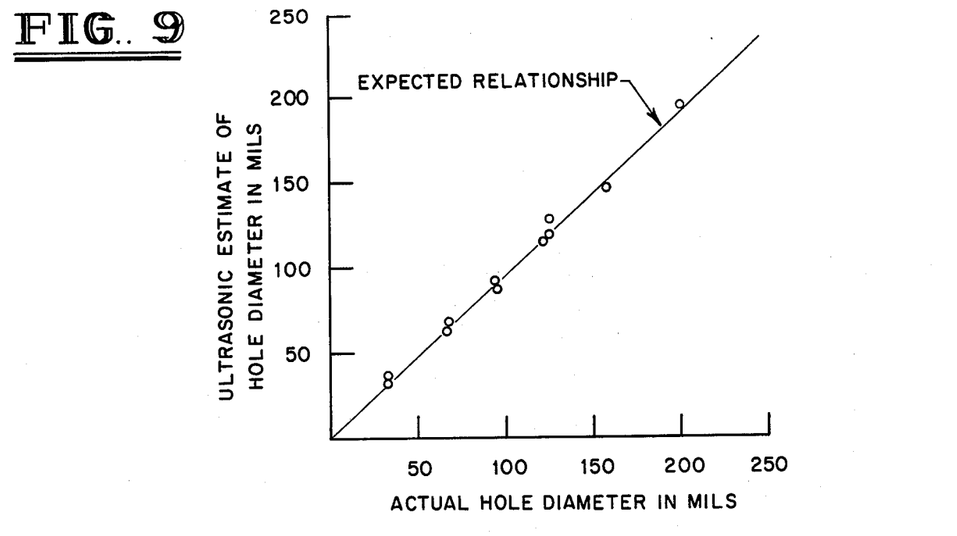
FIG. 9 shows an experimentally found approximate one-to-one correspondence between the ultrasonically predicted and visually determined side-drilled-hole diameters.

FIGS. 7 and 8 illustrate the self-calibration procedure that may be performed right on the work piece (i.e. without having notches and/or side-drilled holes available in a separate calibration block) with a 45-degree shear wave. The product of the calibration delay time between the first two corner-reflected pulses from the end of a plate or pipe specimen of thickness h with the shear wave velocity is given by $$c\Delta_h = 1.41 h \quad (4)$$

Division of Equation (4) by Equation (3) for $\Delta_o = d_o$ yields the calibration equation for sizing void-like defects in carbon steel 1020

$$\Delta_h = 0.52 h \quad (5)$$

Therefore, if the time scale of the oscilloscope is set to read 0.52h units between the first two reflections from the test specimen's end, or from the end of a plain piece of similar material, the diameter of the void can be read directly in mils or millimeters on the oscilloscope screen, regardless of the bearing angle $\beta$ of the ultrasonic beam. The constant of the calibration equation changes only slightly from one metal to another.

Figure 10:
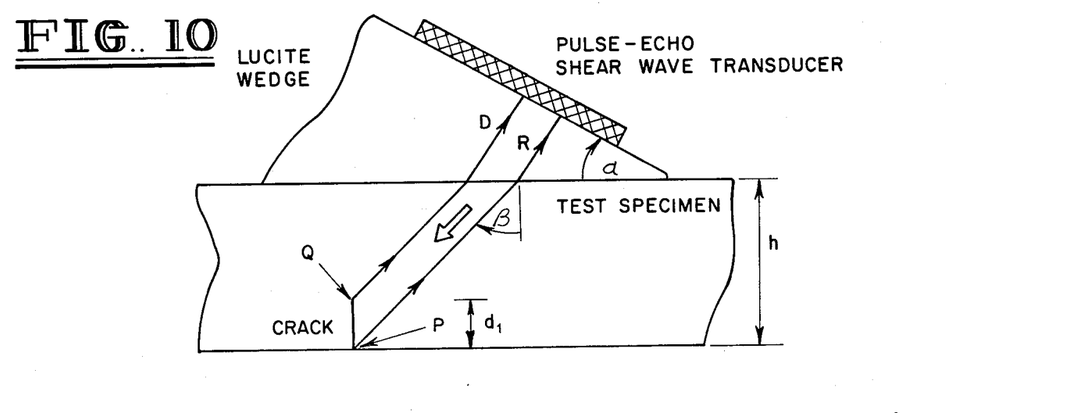
FIG. 10 shows the interaction of an ultrasonic shear wave having a bearing angle $\beta$ in a test specimen of thickness h with a crack-like defect resulting in a base-reflected pulse R and a leading tip-diffracted satellite pulse D. The incident wave (hollow arrow) is split into a R component and a D component by a crack of depth $d_l$ having a base at point P and a tip at point Q.
Figure 11:
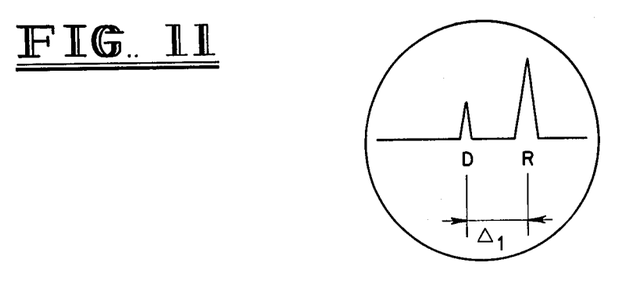
FIG. 11 shows the reflected and diffracted pulses of FIG. 10 separated by delay time $\Delta_l$ on the oscilloscope screen.

The satellite-pulse technique as it is used for sizing crack-like defects is slightly different than that for sizing void-like defects. As shown in FIG. 10, in the crack-sizing position (probe position 5 in FIG. 1) the incident ultrasonic beam is aimed at point Q to maximize the amplitude of the tip-diffracted wave ("D wave"). Upon the incident beam's encountering the base of the crack at point P, a generally stronger reflected wave ("R wave") is sent back to the transducer which arrives after the diffracted pulse as is shown in FIG. 11.

The delay time between the R pulse and its diffracted satellite $\Delta_1$ is a linear function of the depth of the crack $d_1$ as expressed by the relationship $$\Delta_1 = \frac{2 d_1 \cos\beta}{c}$$

where $\beta$ is the bearing angle of incident beam. For a 45-degree beam, we obtain $$c\Delta_1 = 1.41 d_1 \quad (7)$$

The first two reflections from the test specimen's end, or from the end of a plate of similar composition, may again be used to eliminate the influence of the shear wave velocity on the linear relationship between $d_1$ and $\Delta_1$ in Equation (7). FIGS. 7 and 8 illustrate the self-calibration procedure that may be performed right on the work piece (i.e. without having notches and/or side-drilled holes available in a separate calibration clock) with a 45-degree shear wave. The calibration delay time between the first two corner-reflected pulses of a plate or pipe sepcimen of thickness h is given by Equation (4). Division of Equation (4) by Equation (7) for $\Delta_1 = d_1$ yields the calibration equation for sizing crack-like defects in any metal $$\Delta_h = h \quad (8)$$

Therefore, if the time scale of the oscilloscope is set to read h units between the first two reflections from the test specimen's end, or from the end of a plain of similar material, the depth of the crack can be read directly in mils or millimeters on the oscilloscope screen, provided that the examination is carried out with a 45-degree shear wave.

Because the satellite-pulse technique is independent of pulse amplitude for characterizing the anomaly, and because wave speed does not vary significantly within most classes of metals, a reasonably accurate calibration can be made by applying the calibration results obtained upon another piece of similar metal. In practice, the types of metal to be tested will be known, and predetermined wave speed data from similar such metals may be used to quickly calibrate the device without running any on-site tests.

It should be noted that the above description has been presented in a simplified form to facilitate conveying the working principles of the method. As defects have innumerable geometries and locations, often multiple satellite pulses will be obtained. In this event, the satellite pulse having the largest separation in time-of-arrival (delay time) between it and the main reflected pulse should be selected to find the maximum size of the defect. For volumetric defects this will be last satellite pulse to arrive and for planar defects the first satellite pulse to arrive. Also the delay time between the remaining satellite pulses and the main reflected pulse may be used to determine dimensions of the defect which are smaller than those associated with the satellite having the greatest delay time.

Figure 12:
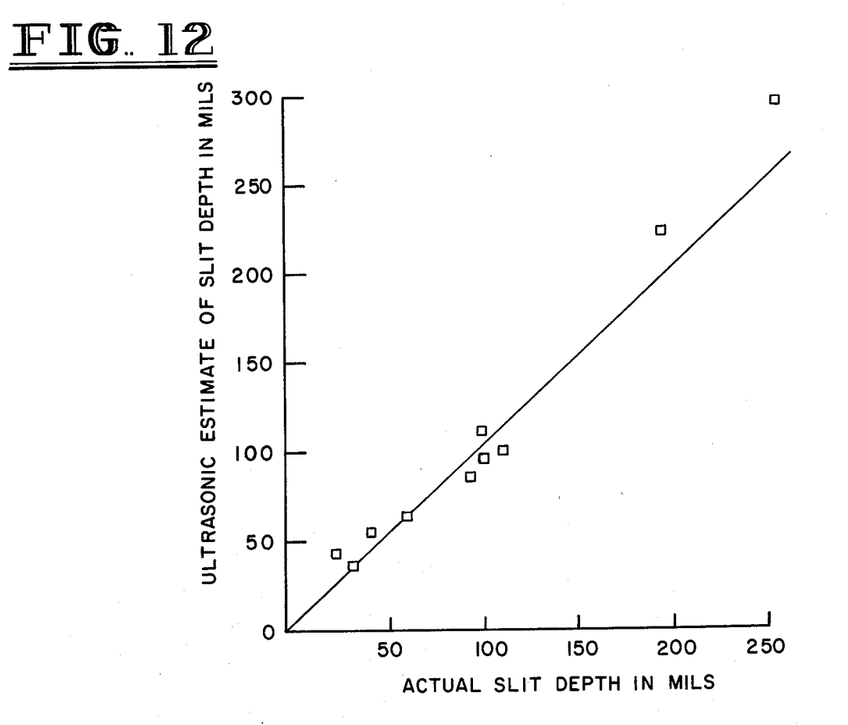
FIG. 12 shows an experimentally found approximate one-to-one correspondence between the ultrasonically predicted and visually determined slit depths.

Notches and steps were used in proof-of-principle measurements since their depth could be determined visually without breaking open the test specimens. The results shown in FIG. 12 were obtained by using 45- and 60-degree shear-wave probes and a range of frequencies (2 to 4 MHz) and defect locations (0.05 to 2 inches) in six different steel specimens with otherwise unspecified acoustical properties. The ultrasonic estimates of slit depth compare very favorable with visual measurements of slit depth.

Figure 13:
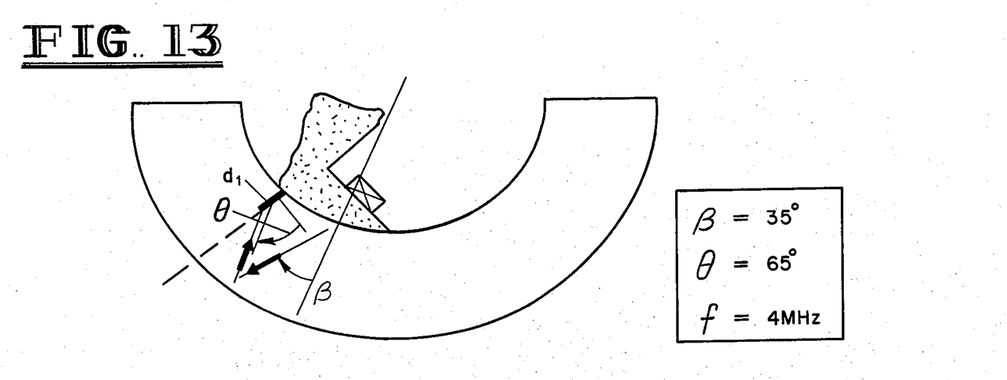
FIG. 13 shows the probe position for direct sizing of a fatigue crack of depth $d_l$ in a turbine rotor specimen from the accessible surface by the satellite-pulse technique. The frequency of the ultrasound is denoted by f, and $\Theta$ denotes the angle the beam makes with the line drawn perpendicularly to the plane of the crack.
Figure 14:
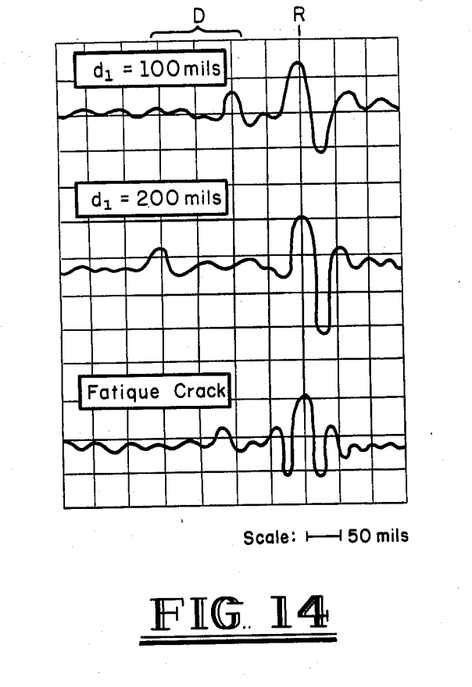
FIG. 14 shows the FIG. 13 tip-diffracted pulses D preceding base-reflected pulses R in the composite ultrasonic signature of narrow slits (upper and middle traces) and the fatigue crack (lower trace).

The satellite-pulse technique has now been used to size a number of laboratory and service-induced fatigue and intergranular stress corrosion cracks. The results for a laboratory-produced fatigue crack in a carbon steel turbine rotor specimen are shown in FIGS. 13 and 14. The methods illustrated in FIGS. 13 and 14 yielded depth estimates for the fatigue crack at its deepest midlength point of 115 mils. The fatigue crack has not been sectioned.

The equation for determining $d_1$ upon a curved test specimen such as is shown in FIG. 13 is derived from an expression more generally applicable than Equation (6).

$$\Delta_1 = \frac{2d_1 \sin \theta}{c} \qquad (9)$$

FIG. 13 shows how the method which may be used to identify and size defects from probe positions which may be inaccessible by other testing methods. FIG. 14 illustrates the direct readout of a defect's size on the screen of a calibrated oscilloscope. Because the delay time between the times-of-arrival for the satellite pulse and the main reflected pulse is practically independent of the probe-to-defect distance, many different approaches to obtaining data are available, such as reflecting the incident beam off of anterior walls to achieve more practicable accesses to the defect. The technique may, therefore, be used to characterize defects which were previously thought to be inaccessible.

Although the satellite-pulse technique may be used for volumetric defects other than voids, radiographic methods of determining the density of such defects are available and preferably will be used to determine the defect/body density contrast prior to sizing by the satellite-pulse technique. Although many currently used ultrasonic test methods are limited to the use of only shear waves or alternatively, only longitudinal waves, the disclosed method may profitably be used in connection with either type of wave. Shear waves are preferably used because of the better resolution provided.

Because the disclosed methods depend upon accurate separation of the returning pulse pairs, the ultrasonic transmitter should be capable of a high frequency transmission having a broad frequency range; the receiver should be capable of a high frequency transmission having a broad frequency range; and the resolving unit a reasonably high resolution instrument. Detection of and measurement between the different reflected, scattered and diffracted pulses may be done either with or without signal averaging techniques and digital readout devices.

In view of the improved defect discrimination and sizing ability offered by the satellite-pulse technique, it will be preferable in the future to replace the sole use of the peak amplitude of the reflected pulse for defect characterization with reliance upon methods utilizing separation in times-of-arrival between resolved pulse components of the composite defect signal as described above.

The invented method's use of pattern recognition for identifying defects of arbitrary shape frees it from dependence upon returning pulse amplitude measurements and from dependence upon probe-to-defect distance measurements. By moving the probe about the defect and aiming the incident beam at the defect extremities (probe positions 5 in FIG. 1 or 3) as described above, sufficient information can be gained from returning pulses to permit application of the above described pattern recognition method of defect identification and the above described delay time method of defect sizing. The speed with which ultrasonic waves travel within metal varies much less between different types and grades of metals than does the attenuation of such waves. Thus by relying upon separation in time-of-arrival as the variable in sizing the defect rather than upon amplitude as do current methods, a more readily calibration and more reliable method is disclosed. Furthermore, once the type of metal to be tested is known, the testing apparatus may be calibrated prior to being taken to the test location and additionally will be calibrated for all further tests upon similar metal without recalibration.

The satellite-pulse technique above described, (1) in step one detects, resolves, recognizes and permits discrimination of a satellite pulse from ghost satellite pulses and general background interference, (2) in step two identifies the defect as either planar or volumetric based upon the arrival of the satellite pulse relative to the main reflected pulse or, if no true satellites exist, finds the reflector to be a geometrical reflector in the test specimen and not a defect, and (3) in step three sizes the defect to find $d_o$ or $d_1$ based upon the delay time between the reception of the satellite pulse and the main reflected pulse.

It is apparent that the method's independence of detected pulse amplitude and probe-to-defect distance, its ability to permit the operator to freely move the probe and other advantages apparent from the above description are significant improvements in the art of nondestructive testing.

While the invention has been described in connection with the preferred embodiment, it is not intended to limit the invention to the particular forms set forth, but, on the contrary, it is intended to cover such alternatives, modifications and equivalents as may be included within the spirit and scope of the invention as defined by the appended claims.

What is claimed is:

1. An ultrasonic test method using a test unit to identify an anomaly within a body as either a substantially planar anomaly or a substantially volumetric anomaly comprising the steps of:
   (a) transmitting by means of a transducer an ultrasonic incident wave within said body to interact with said anomaly and create at least one reflected wave and at least one satellite wave;
   (b) receiving by means of a transducer a portion of a reflected wave and a portion of a satellite wave;
   (c) resolving by means of a resolution unit said received waves to produce a reflected wave component and a satellite wave component;
   (d) detecting whether reception of said satellite wave component occurs prior to or after reception of said reflected wave component; and
   (e) identifying said anomaly as substantially planar or as substantially volumetric depending upon the reception sequence of said reflected wave component and said satellite wave component.

2. The method of claim 1 wherein said anomaly is identified as substantially planar if reception of said satellite wave component occurs prior to reception of said reflection wave component.

3. The method of claim 1 wherein said anomaly is identified as substantially volumetric if reception of said satellite wave component occurs after reception of said reflection wave component.

4. An ultrasonic test method using a test unit to identify an anomaly within a body as a substantially planar anomaly or a substantially volumetric anomaly comprising the steps of:

(a) transmitting, by means of a transducer located at a first position, an ultrasonic incident wave within said body to interact with said anomaly and create at least one reflected wave and at least one satellite wave;

(b) receiving by means of a transducer a portion of a reflected wave and a portion of a satellite wave;

(c) resolving by means of a resolution unit said received waves to a reflected wave component and a satellite wave component;

(d) measuring the difference between the reception time for said reflected wave component and the reception time for said satellite wave component to produce a first delay time;

(e) repeating steps (a), (b), (c), and (d) with a transducer located at least one additional position having a different incident wave bearing angle with regard to said anomaly to produce at least one additional delay time;

(f) detecting whether said delay times vary or do not vary as a function of changing said bearing angle;

(g) identifying said anomaly as being substantially planar or substantially volumetric depending upon the functional relationship between said delay times and said bearing angles.

5. The method of claim 4 wherein said anomaly is identified as substantially planar if said delay times vary as a nonlinear function of changing said bearing angle.

6. The method of claim 4 wherein said anomaly is identified as substantially volumetric if said delay times do not vary as a function changing said bearing angle.

7. The method of claims 1 or 4 further comprising:

(a) recognizing said reflected wave component by detecting said reflected wave component's large energy content relative to other received wave components; and (b) recognizing said satellite wave component by eliminating all wave components received prior to said reflected wave component which prior wave components do not have a dissynchronous relative energy content pattern with said reflected wave component and eliminating all wave components received subsequent to said reflected wave component which subsequent wave components do not have a synchronous relative energy content pattern with said reflected wave component, a remaining wave component associated with said reflected wave component, if any, being a satellite wave component.

8. The method of claim 7 additionally comprising maximizing the energy content of said received portion of said satellite wave component relative to the energy content of all other received waves to facilitate recognition of said satellite pulse and identification of said anomaly.

9. An ultrasonic test method for sizing an anomaly within a test body comprising the steps of:

(a) transmitting by means of a transducer an ultrasonic indicent wave within said body to interact with said anomaly and create at least one reflected wave and at least one satellite wave;

(b) receiving by means of a transducer a portion of said reflected wave and a portion of said satellite wave;

(c) resolving by means of a resolution unit said received waves into a reflected wave component and a satellite wave component;

(d) measuring the difference between the reception time for said reflected wave component and the reception time for said satellite wave component to produce a delay time; and (e) sizing said anomaly by using said delay time as a proportional indicator of anomaly size.

10. The method of claim 9 further comprising:

(a) recognizing said reflected wave component by detecting said reflected wave component's large energy content relative to other received wave components; and (b) recognizing said satellite wave component by eliminating all wave components received prior to said reflected wave component which prior wave components do not have a dissynchronous relative energy content pattern with said reflected wave component and eliminating all wave components received subsequent to said reflected wave component which subsequent wave components do not have a synchronous relative energy content pattern with said reflected wave component, a remaining wave component associated with said reflected wave component, if any, being a satellite wave component.

11. The method of claim 9 additionally comprising:

(a) identifying said anomaly as being substantially volumetric;

(b) recognizing a satellite wave component as a scattered wave component derived from scattered waves by detecting reception of said satellite wave component as subsequent to reception of said reflected wave component;

(c) measuring the difference between the reception time for said reflected wave component and the reception time for said scattered wave component to produce a scattered wave delay time; and (d) sizing said anomaly by using said scattered wave delay time as a proportional indicator of a diameter of said anomaly.

12. The method of claim 11 additionally comprising facilitating said measurement by aiming said incident wave to maximize said scattered wave component.

13. The method of claim 9 additionally comprising:

(a) identifying said anomaly as being substantially volumetric;

(b) measuring the difference between the reception time for said reflected wave component and the reception time for said satellite wave component received later than all other satellite wave components associated with said reflected wave component to produce a postcursor delay time; and (c) sizing said anomaly by using said postcursor delay time as a proportional indicator of said anomaly's maximum diameter.

14. The method of claim 13 additionally comprising facilitating said measurement by aiming said incident wave to maximize the satellite wave component corresponding to back scattered waves from about said anomaly.

15. The method of claim 11 additionally comprising:

(a) limiting reception of said scattered waves to those said scattered waves which are reradiated from about said volumetric anomaly in a direction substantially parallel to that of said incident wave; and (b) using a single probe to transmit said incident waves, receive said reflected waves and receive said limited scattered waves.

16. The method of claim 11 wherein said sizing of said anomaly additionally comprises expressing the diameter of said volumetric anomaly as a function of said scattered wave delay time multipled by $$\frac{1}{\frac{\pi}{2v} + \frac{1}{c}}$$

where c is the velocity of the incident wave within said body and v is the Rayleigh wave velocity of said scattered wave about said defect.

17. The method of claim 7 additionally comprising:
   (a) identifying said anomaly as being substantially planar;
   (b) recognizing a satellite wave component as a diffracted wave component derived from diffracted waves by detecting reception of said satellite wave component as prior to reception of said reflected wave component;
   (c) measuring the difference between the reception time for said reflected wave component and the reception time for said diffracted wave component to produce a diffracted wave delay time; and
   (d) sizing said anomaly by using said diffracted wave delay time as a proportional indicator of said anomaly's depth.

18. The method of claim 17 wherein said incident wave is aimed to substantially maximize the energy received from said satellite waves created by tip diffraction at an extremity of said anomaly and wherein a single probe is used to transmit said incident waves, receive said received portion of said reflected waves, and receive said received portion of said diffracted waves.

19. The method of claim 17 wherein sizing of said anomaly additionally comprises expressing the depth of said planar anomaly as a function of said diffracted wave delay time multiplied by $$\frac{c}{2 \cos \beta}$$

where c is the velocity of the incident wave within said body and $\beta$ is the bearing angle of said incident wave.

20. The method of claim 17 wherein said sizing additionally comprises using the satellite wave component associated with said reflected wave component and received earlier than all other such satellite wave components as the satellite wave component from which a precursor delay time is measured, said precursor delay time being proportional to the maximum depth of said planar anomaly.

21. The method of claim 9 additionally comprising calibrating said test unit to facilitate sizing said anomaly from said delay time.

22. The method of claim 21 wherein said calibration comprises:
   (a) transmitting calibration waves within said body by means of a transducer;
   (b) receiving said calibration waves by means of a transducer;
   (c) measuring a calibration delay time between said calibration waves; and
   (d) calibrating said resolution unit to substantially eliminate the influence of wave velocity within said body upon a delay-time-to-anomaly-size relationship by using said calibration delay time.

23. The method of claim 22 additionally comprising:
   (a) calibrating said resolution unit for a constant bearing angle for said incident waves; and
   (b) using said constant bearing angle for sizing said anomaly within said body to permit adjustment of a wave time-of-arrival measurement device to display data having a linear relationship to said anomaly size.

24. The method of claim 22 wherein said incident waves, said received reflected waves, said received scattered or diffracted waves, and said calibration waves are transmitted and received by a single probe.

25. The method of claim 21 additionally comprising calibrating said resolution unit upon a calibration body of similar composition to said test body to facilitate sizing said anomaly within said test body.

26. The method of claim 25 wherein said calibration includes:
   (a) selecting a calibration body of similar composition to said test body;
   (b) transmitting calibration waves within said calibration body by means of a transducer;
   (c) receiving said calibration waves by means of a transducer;
   (d) measuring a calibration delay time between said calibration waves; and
   (e) calibrating said resolution unit to substantially eliminate the influence of said wave velocity within said test body upon a delay-time-to-anomaly-size relationship by using said calibration delay time.

27. An ultrasonic test method using a resolution unit to identify reflected waves received from the test specimen's boundaries as being indicative of test specimen geometry rather than an anomaly within said test specimen comprising the steps of:
   (a) transmitting by means of a transducer an ultrasonic wave within said test specimen to interact with a suspected anomaly and create at least one reflected wave and at least one satellite wave; and
   (b) identifying said suspected test specimen anomaly as corresponding to test specimen geometry rather than an anomaly if no satellite waves are created by said interaction of said ultrasonic wave with said suspected anomaly.

28. An ultrasonic test method of identifying and sizing an anomaly within a body comprising:
   (a) initially aiming an ultrasonic beam from a probe in the general direction of said anomaly to create, through a transducer, a main reflected pulse and at least one satellite pulse, together with such ghost satellite pulses, and general background interference pulses as may be created;
   (b) recognizing said main reflected pulse by detecting said main reflected pulse's large amplitude relative to all other pulses;
   (c) recognizing as associated pulses pulses detected to vary in amplitude or time-of-arrival as a function of the changing amplitude and time-of-arrival of said main reflected pulse upon changing the position of said probe and recognizing all other pulses as ghost satellite pulses or as general background interference pulses;
   (d) recognizing as satellite pulses pulses received prior to said main reflected pulse which have a dissynchronous relative amplitude pattern with said main reflected pulse and pulses received subsequent to said main reflected pulse which have a synchronous relative amplitude pattern with said main pulse;

(e) identifying said anomaly as substantially planar if the satellite pulse is received prior to said main reflected pulse and identifying said anomaly as substantially volumetric if the satellite pulse is received subsequent to said main reflected pulse;

(f) secondly aiming said ultrasonic beam to maximize the amplitude of the satellite pulse received prior to all other satellite pulses if said anomaly is identified as planar and secondly aiming said ultrasonic beam to maximize the amplitude of the satellite pulse received after all other satellite pulses if said anomaly is identified as volumetric;

(g) measuring the difference between the time-of-arrival of said main reflected pulse and the time-of-arrival of said maximized satellite pulse to produce a delay time; and (h) sizing said anomaly by using said delay time as a proportional indicator of anomaly size.

29. The method of claim 28 additionally comprising aiming said ultrasonic beam to first reflect from a reflector within said body other than said anomaly and secondly interact with said anomaly to produce said main reflected pulse, said at least one satellite pulse, and said ghost pulses.

* * * * *